United States Patent
Pathak et al.

(10) Patent No.: US 8,313,770 B2
(45) Date of Patent: Nov. 20, 2012

(54) MODIFYING DRUG RELEASE IN SUSPENSIONS OF IONIC RESIN SYSTEMS

(75) Inventors: Yashwant Vishnupant Pathak, Louisville, KY (US); Russell Lee McMahen, Flower Mound, TX (US); Mark Tengler, Colleyville, TX (US)

(73) Assignee: NEOS Therapeutics, LP, Grand Prairie, TX (US)

( * ) Notice: Subject to any disclaimer, the term of this patent is extended or adjusted under 35 U.S.C. 154(b) by 325 days.

(21) Appl. No.: 12/130,762

(22) Filed: May 30, 2008

(65) Prior Publication Data

US 2009/0011027 A1 Jan. 8, 2009

Related U.S. Application Data

(60) Provisional application No. 60/940,956, filed on May 30, 2007.

(51) Int. Cl.
*A61K 9/10* (2006.01)
*A61K 31/74* (2006.01)

(52) U.S. Cl. .................. 424/486; 424/78.1

(58) Field of Classification Search .......... 424/486, 424/470, 78.1
See application file for complete search history.

(56) References Cited

U.S. PATENT DOCUMENTS

| | | | |
|---|---|---|---|
| 2,793,203 A * | 5/1957 | Schultze et al. ........ 530/389.5 |
| 3,173,876 A | 3/1965 | Zobrist |
| 3,276,586 A | 10/1966 | Rosaen |
| 3,541,005 A | 11/1970 | Strathmann et al. |
| 3,541,006 A | 11/1970 | Bixler et al. |
| 3,546,142 A | 12/1970 | Michaels et al. |
| 4,221,778 A | 9/1980 | Raghunathan |
| 4,285,987 A | 8/1981 | Ayer et al. |
| 4,692,462 A * | 9/1987 | Banerjee ............ 424/444 |
| 4,762,709 A | 8/1988 | Sheumaker |
| 4,999,189 A * | 3/1991 | Kogan et al. ........ 424/493 |
| 5,980,882 A | 11/1999 | Eichman |
| 5,980,945 A | 11/1999 | Ruiz |
| 6,120,787 A | 9/2000 | Gustafsson et al. |
| 6,613,358 B2 | 9/2003 | Randolph et al. |
| 2003/0124184 A1 * | 7/2003 | Mezaache et al. ......... 424/465 |
| 2005/0013792 A1 * | 1/2005 | Hollenbeck et al. ...... 424/78.1 |
| 2007/0092553 A1 * | 4/2007 | Tengler et al. .......... 424/440 |

OTHER PUBLICATIONS

Hänninen et al. (Journal of Controlled Release 91 (2003) 449-463.*
International Search Report and Written Opinion for PCT/US2008/065408 dated Sep. 16, 2008.

* cited by examiner

*Primary Examiner* — Aradhana Sasan
(74) *Attorney, Agent, or Firm* — Hunton & Williams, LLP

(57) ABSTRACT

The present invention includes compositions and methods for delivering one or more unit dosage units by modifying the release profile of an optionally coated drug-resin complex suspended in an ionic salt solution, wherein the optionally coated drug-resin complex includes one or more active agents loaded on to one or more ion-exchange resin particles, and wherein the release of the one or more active agents is modulated by the one or more ionic salts in solution.

28 Claims, 2 Drawing Sheets

MODIFYING DRUG RELEASE IN SUSPENSIONS OF IONIC RESIN SYSTEMS

CROSS-REFERENCE TO RELATED APPLICATIONS

This application claims priority to U.S. Patent Application Ser. No. 60/940,956, filed May 30, 2007, the entire contents of which are incorporated herein by reference.

TECHNICAL FIELD OF THE INVENTION

The present invention relates in general to the field of compositions and methods of making and modifying liquid, sustained-release formulations, and more particularly, to the use of methods that eliminate the problems associated with the manufacture of the same.

BACKGROUND OF THE INVENTION

Without limiting the scope of the invention, its background is described in connection with liquid sustained release suspensions.

One such method of making sustained release particles is taught in U.S. Pat. No. 6,120,787, issued to Gustafsson, et al., which teach a method of preparing parenterally administrable sustained release microparticles, that include preparing core particles in an aqueous medium that is essentially free from organic solvent, a biologically active substance being entrapped therein during or after said preparation, drying the core particles and coating the same with a release-controlling polymer by air suspension technique so as to create a shell on the core particles without any detrimental exposure of the active substance to organic solvent.

Another sustained-release composition includes an amorphous polymer are taught in U.S. Pat. No. 6,613,358, issued to Randolph, et al., which provided for a sustained release composition for sustained release of a pharmaceutical substance that includes a biocompatible polymer that is highly amorphous and a pharmaceutical substance in a hydrophobic ion complex with an amphiphilic material. A compressed antisolvent method for manufacturing the composition it taught as are various product forms incorporating the composition and various uses for the composition.

Yet another sustained release drug formulation is taught in U.S. Pat. No. 5,980,945, issued to Ruiz in which a sustained release drug formulation includes a drug; a biodegradable polymer that is insoluble in water; and an oil vehicle in which both the drug and the polymer are dissolved. The oil vehicle contains 10-100% by volume of a pharmaceutically acceptable oil and 0-90% by volume a pharmaceutically acceptable liquid carrier for the drug or the polymer.

Despite these advances the release of the drug from the ion resin system is modified by coating the resin conjugates. There are several products on the market in both the solid form and as a liquid suspension that use this technology. This new invention describes a simple but very effective technique that can be used to alter the drug release from the ion resin system using the addition of suitable salts. It also describes the impact of salt addition, in the suspension formulations of drug resin conjugates, on the drug release profiles. This technique can be used to modify and manipulate the drug release profiles from the ion resin system.

SUMMARY OF THE INVENTION

The present invention addressed the problems associated with the delivery of one or more active agents in ion resin form under controlled conditions and methods for modifying the same before and/or after manufacture in liquid, gum or dry states. The present invention includes compositions and methods for modifying the drug release of suspensions that use the coated ion exchange resin drug complex delivery system, through the use of additional ionic materials. Liquid formulations are preferred by many users due to the ease of delivery, namely, swallowing thereby leading to increased compliance with dosing regimens. It has been found that many children and adults fail to comply with dosing instructions due to the size, shape, taste and/or mouth-feel of, e.g., tablets, caplets and even gelcaps.

The present inventors have recognized that delivery of agents in liquid formulation is not only preferred by many users, but also that many of the materials and processing methods and equipment using in the industry today fail to deliver products and formulations that delivery the active agents in doses and time that are consistent. Furthermore, the compositions must also be shelf-stable, do not separate on the shelf (both floating and settling), do not require vigorous shaking (which greatly affects dosing consistency), the mouth-feel of the liquid (e.g., grainy, bitter, slimy), provide actual controlled, sustained, mixed or modified release. Finally, it was recognized that despite many decades of research and development, controlled-release formulations have not been amenable to large-scale production in facilities and to amounts that are permissible for industrial applicability of controlled-release liquid formulations.

Ion exchange resins have been used as a carrier for drugs and several products have been marketed using this technology. The problem with the ion resin technology is that the release of the drug from the ion exchange resin conjugate only happens in an ionic environment where some other ionic moiety is present to substitute drug from the resin conjugate. It is also observed that the initial release of the drug is delayed due to non availability of the ionic moiety, leading to inconsistency in drug release profiles. The release of the drug in the first hour to a desired level and the subsequent sustained release of the drug in following hours can be achieved by properly maintaining the concentration of the ionic moiety in the system. The present invention permits the manufacturer of the composition to achieve a desired initial release of the drug from the resin drug conjugate and the effects of the subsequent sustained release over a period of time with greater consistency. Furthermore, the present invention allows the user to modify a release profile even after the manufacture of the material, thereby improving the consistency of the release profile post-manufacture. Alternatively, the physician may direct a pharmacist to alter the release profile by the addition of simple, pharmaceutically acceptable salts.

More particularly, the present invention includes a composition and methods for making a unit dosage form that includes, an optionally coated drug-resin complex suspended in an ionic salt solution, wherein the optionally coated drug-resin complex has one or more active agents loaded on to one or more ion-exchange resin particles, and wherein the release of the one or more active agents is modulated by the one or more ionic salts. The one or more drug-ionic resins are optionally coated with a water-permeable diffusion barrier. In one embodiment, substantially all of the one or more drug-ionic resins are coated with a water-permeable diffusion barrier. Modulation of the release of the active is accomplished by changing the ionic strength of the underlying solution using one or more ionic salts that are increased or decreased in the final storage or delivery solution. The ionic salt may be an inorganic salt, an organic salt, an ionic salt that is different from a salt complexed with the active-agent-to-resin particle complex (e.g., before, during or even after suspension of the active agent-resin complex). In one example, the ionic salts in the solution are reduced with a chelation agent to modify the release profile. In one embodiment, the modification of the release is a more rapid release of one active agent.

Another embodiment of the present invention is a pharmaceutical composition in unit dosage form that includes a first pharmacologically active drug and a second bound to one or more ion-exchange resin particles to form a drug-resin complex, one or more ionic salts in contact with the drug-resin complex, a water-permeable diffusion bather applied to the drug-resin complex, wherein the release of the one or more pharmacologically active drugs is modulated by the one or more ionic salts.

In yet another embodiment, the present invention is a single dose pharmaceutical composition that includes a modifiable release matrix having one or more ionic salts in contact with one or more ion-exchange resin particles bound to one or more pharmacologically active drugs; a water-permeable diffusion barrier applied to the modifiable release matrix; and a solution comprising additional ionic salts, wherein the addition of the ionic salts is controlled to modify the release profile of the active drugs.

Another embodiment includes a single dose pharmaceutical composition with a modifiable release matrix having one or more ionic salts in contact with one or more ion-exchange resin particles bound to one or more pharmacologically active drugs; a water-permeable diffusion barrier applied to the modifiable release matrix; and a solution comprising additional ionic salts, wherein the addition of the ionic salts is controlled to modify the release profile of the active drugs.

The pharmaceutical composition of the present invention may be provided in unit dosage form with one or more drug-ionic resins loaded with one or more pharmacologically active drugs and suspended in a solution having one or more ionic salts, wherein the ionic strength of the one or more ionic salts modulated the release of the one or more pharmacologically active drugs. The one or more drug-ionic resins may be optionally coated with a water-permeable diffusion barrier. In another embodiment, substantially all of the one or more drug-ionic resins are coated with a water-permeable diffusion barrier.

Another embodiment is a pharmaceutical composition in unit dosage form with at least a first pharmacologically active drug and a second pharmacologically active drug loaded on an ionic resins and suspended in a solution comprising one or more ionic salts, wherein the ionic strength of the one or more ionic salts modulated the release of the first pharmacologically active drug, the second pharmacologically active drug or both.

The present invention also includes a method for preparing or modifying a pre-made controlled-release composition by suspending in a carrier one or more ionic salts and one or more pharmacologically active agents loaded on one or more ionic resins, wherein the ionic strength of the one or more ionic salts modulates the release of the one or more pharmacologically active drugs. The one or more ionic resins comprise a water-permeable diffusion barrier, e.g., substantially all of the one or more ionic resins are coated with a water-permeable diffusion barrier.

Yet another method for modifying the release of a drug-resin composition includes adjusting the ionic strength of one or more ionic salts in a solution comprising one or more ionic salts and one or more drug-ionic resin complexes loaded with one or more pharmacologically active drugs, wherein the ionic strength of the one or more ionic salts modulates the release of the one or more pharmacologically active drugs.

The one or more drug-ionic resin complexes are coated optionally with a water-permeable diffusion barrier and the ionic strength of the one or more ionic salts is increased or decreased. In one embodiment, the one or more pharmacologically active drugs comprise an immediate release pharmacologically active drug and an extended release active drug. In another embodiment, the drug-ionic resin complexes may also include a water-permeable diffusion barrier comprising an enteric coat, a resin coat, a lacquer coat, a pH-sensitive coating, a biodegradable polymer matrix, a water soluble matrix, an ionic matrix, combinations and mixtures thereof. The drug-ionic resin complexes may be one or more polymers selected from the group consisting of cellulose, ethylcellulose, methylcellulose, propylcellulose, methoxypropylcellulose, cellulose nitrate, poly(vinyl alcohol), poly (vinyl chloride), polystyrene, polyethylene, polypropylene, poly(ethylene-co-vinyl acetate), poly(hydroxybutyric acid), poly(hydroxyvalerianic acid-co-hydroxybutyric acid), poly (lactic acid), poly(glycolic acid), poly(lactic acid-co-glycolic acid), poly($\epsilon$-caprolactones), poly($\epsilon$-caprolactone-co-DL-lactic acid), poly(maleic anhydride), polyamides, gelatin, chitosan, collagen, poly(hydroxyalkyl)-L-glutamines, poly ($\gamma$-ethyl-L-glutaminate-co-glutamic acid), poly(L-leucine-co-L-aspartic acid), poly(proline-co-glutamic acid), poly (alkyl 2-cyanoacrylates), polyurethanes, poly(methyl methacrylate), poly(methyl methacrylate-co-methacrylic acid) and poly(methacrylate-co-hydroxypropyl methacrylate), polystyrene, polistirex, salts, combinations and mixtures thereof.

Examples of active agents that may be provided as part of the liquid formulations of the present invention include vitamins, minerals, nutritional supplements, herbal extracts, gums, gels, oils, salts, mixtures and combinations thereof. Pharmaceutical active agents may include, e.g., protein, peptide, carbohydrate, polysaccharide, glycoprotein, lipid, hormone, growth factor, cytokine, interferon, receptor, antigen, allergen, antibody, antiviral, antifungal, antihelminthic, substrate, metabolite, cofactor, inhibitor, drug, nutrient, toxin, poison, explosive, pesticide, chemical warfare agent, biowarfare agent, biohazardous agent, infectious agent, prion, radioisotope, vitamin, heterocyclic aromatic compound, carcinogen, mutagen, narcotic, amphetamine, barbiturate, hallucinogen. In some cases the liquid may be, eg., a vaccine for against a virus, bacterium, helminth and/or fungi, fragments, receptors or toxins thereof, e.g., *Salmonella, Streptococcus, Brucella, Legionella, E. coli, Giardia, Cryptosporidium, Rickettsia*, spore, mold, yeast, algae, amoebae, dinoflagellate, unicellular organism, pathogen, cell, combinations and mixtures thereof. The one or more active agents may be a pharmaceutical agent, an enzyme, a cytokine, a growth promoting agent, an antibody, an antigen, a hormone, a vaccine, a cell, a live-attenuated pathogen, a heat-killed pathogen, a virus, a bacteria, a fungi, a peptide, a carbohydrate, a nucleic acid, a lipid, mixtures and combinations thereof.

Specific examples of active agents include: steroids, respiratory agents, sympathomimetics, local anesthetics, antimicrobial agents, antiviral agents, antifungal agents, antihelminthic agents, insecticides, antihypertensive agents, antihypertensive diuretics, cardiotonics, coronary vasodilators, vasoconstrictors, $\beta$-blockers, antiarrhythmic agents, calcium antagonists, anti-convulsants, agents for dizziness, tranquilizers, antipsychotics, muscle relaxants, drugs for Parkinson's disease, respiratory agents, hormones, non-steroidal hormones, antihormones, vitamins, antitumor agents, miotics, herb medicines, herb extracts, antimuscarinics, interferons, immunokines, cytokines, muscarinic cholinergic blocking agents, mydriatics, psychic energizers, humoral agents, antispasmodics, antidepressant drugs, anti-diabetics, anorectic drugs, anti-allergenics, decongestants, expectorants, antipyretics, antimigrane, anti-malarials, anti-ulcerative, anti-estrogen, anti-hormone agents, anesthetic agent, or drugs having an action on the central nervous system. For example, for use in the treatment of cold/cough symptoms the active agents may include one or more antihistamines, antitussives, expectorants and the like, e.g., pseudoephedrine, chlorpheniramine, dextromethorphan, guaifenesin, and salts thereof or mixtures of salts thereof. The liquid formulation may also include an analgesic or even a narcotic.

Examples of carriers for the actives of the present invention include any degradable, partially degradable or non-degradable and generally biocompatible polymer, e.g., polystirex, polypropylene, polyethylene, polacrilex, poly-lactic acid (PLA), poly-glycolic acid (PGA) and/or poly-lactic polyglycolic acid (PGLA) in the form or a matrix or even a bead.

The present invention also includes those liquid formulations made by the methods disclosed and claimed herein. For example, specific liquid formulation may include one or more active agents available for immediate, modified and/or extended or controlled release for use in treating cold/cough/allergy symptoms. The one or more actives for cold/cough/allergy may include one or more of the following: anti-tussives, anti-histamines, expectorants and analgesics. For example, the actives may include: pseudoephedrine, chlorpheniramine, dextromethorphan, guaifenesin, and salts thereof or mixtures of salts thereof.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
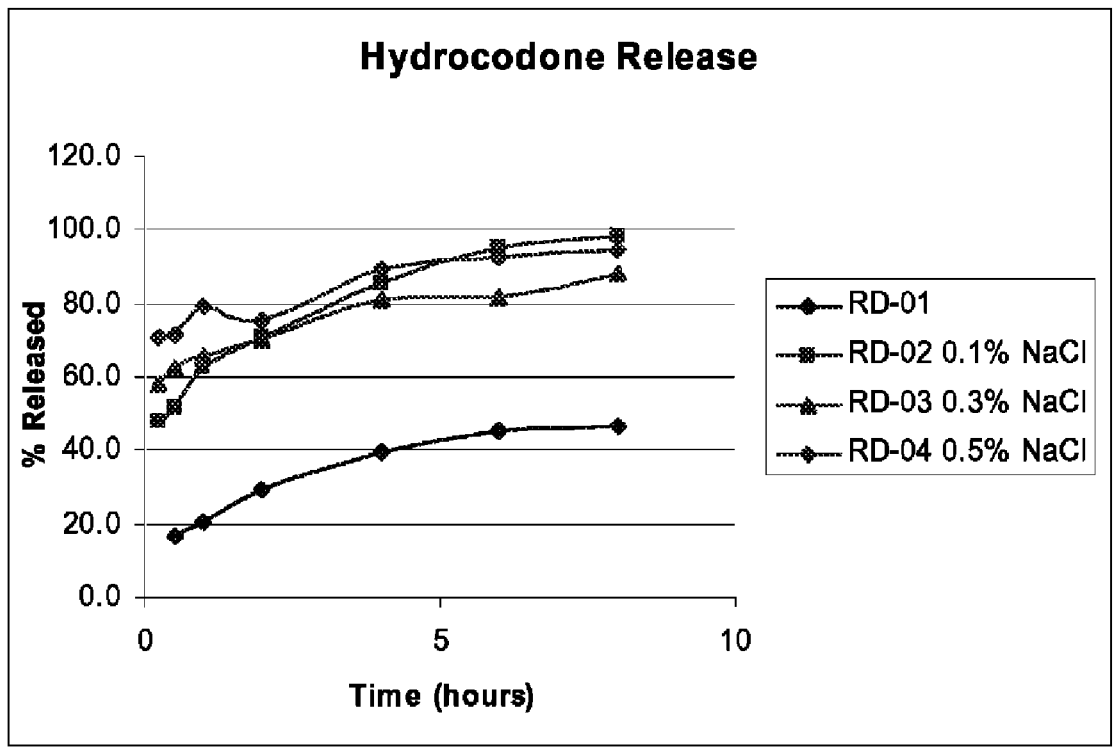
FIG. 1 is a graph that shows the release of the Hydrocodone for 10 hours in a sustained release suspension showing the impact of the added salt on the comparatively faster release of the drug from the coated Hydrocodone Polistirex.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention includes a surprising result obtained from the use of ionic materials in and/or after the formulation of suspensions and solids that use an ion exchange resin(s) as a carrier(s) for both immediate and sustained release of active agents, such as drugs, loaded on the ion exchange resin particles. Importantly, it was also found that the modifications disclosed herein could be made to both coated and uncoated resin particles. Ion exchange resins have been used for the conjugation of drugs using both suspension and solid dose delivery systems. The drug loaded resin is optionally coated with a suitable coating material to control the release of the drug. The coated conjugated drug resin complex may be stored as is (in dry or semi-dry form) and later suspended in a suitable delivery vehicle. In fact, the present invention includes the addition of salts to the dry powder prior to resuspension, during resuspension and/or after resuspension in a suitable vehicle.

Generally, when the ion exchange resin (coated or uncoated) material comes into contact with body fluids in the GI tract, the drug loaded on the resin particle (the drug-resin conjugate) is replaced by the ions present in the body fluids and made available for absorption in the body. The present invention provides additional control of the release of the active agent loaded on the resin by changing the ionic concentration in the suspension itself to modify and assist in manipulating the drug release profile(s) from the system. To demonstrate the change in control, the present inventors studied the impact of various ionic salts added to different ion exchange resin formulations. It was found that the addition of ionic salts at specific levels serve control or modify the release of the drug(s) in vitro and later in vivo. Surprisingly, it was found that the effect would be separated between two different actives, that is, in one case the release profile remained relatively constant while the release profile of the other active was modulated.

Using the methods of the present invention, it was possible to prepare novel formulations as well as modify existing formulations. The methods disclosed herein were used to formulate various suspension products using the ion exchange resin as the drug carrier and incorporating various levels of ionic salts in order to modify the release of the drug(s).

Examples of ionic salts that may be used to modify the release profile of an active-agent-resin particle complex include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate. Another method for defining the ionic salts may be as an acidic functional group, such as a carboxylic acid functional group, and a pharmaceutically acceptable inorganic or organic base. Non-limiting examples of bases include, but are not limited to, hydroxides of alkali metals such as sodium, potassium and lithium; hydroxides of alkaline earth metal such as calcium and magnesium; hydroxides of other metals, such as aluminum and zinc; ammonia; and organic amines, such as unsubstituted or hydroxy substituted mono-, di-, or trialkylamines; dicyclohexylamine; tributylamine; pyridine; N-methyl-N-ethylamine; diethylamine; triethylamine; mono-, bis- or tris-(2-hydroxy-lower alkyl amines), such as mono- bis- or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the terms "extended release," "sustained release," and "delayed release" are used to define a release profile to effect delivery of an active over an extended period of time, defined herein as being between about 60 minutes and about 2, 4, 6, 8, 12 or even 24 hours. Extended release may also be defined functionally as the release of over 80 to 90 percent (%) of the active ingredient after about 60 minutes and about 2, 4, 6 or even 8 hours. Extended release as used herein may also be defined as making the active ingredient available to the patient or subject regardless of uptake, as some actives may never be absorbed by the animal. Various extended release dosage forms may be designed readily by one of skill in art as disclosed herein to achieve delivery to both the small and large intestines, to only the small intestine, or to only the large intestine, depending upon the choice of coating materials and/or coating thickness.

"Extended release" and "delayed release" formulations may be prepared and delivered so that release is accomplished at some generally predictable location in the lower intestinal tract more distal to that which would have been accomplished if there had been no delayed release alterations. A method for delay of release is, e.g., a coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. Polymers and compatible mixtures thereof may be used to provide the coating for the delayed or the extended release of active ingredients, and some of their properties, include, but are not limited to: shellac, cellulose acetate, phthalate, resin, a purified lac (a refined product obtained from the resinous secretion of an insect). Generally, the coating dissolves in media of pH>7.

The pharmaceutical composition and/or the solid carrier particles can be coated with one or more enteric coatings, seal coatings, film coatings, barrier coatings, compress coatings, fast disintegrating coatings, or enzyme degradable coatings. Multiple coatings may be applied for desired performance. Further, one or more of the actives may be provided for immediate release, pulsatile release, controlled release, extended release, delayed release, targeted release, synchronized release, or targeted delayed release. In fact, the formulation may include combinations of typical pharmaceutical actives (e.g., pseudephedrin) and vitamins (e.g., Vitamin C), minerals (Ca, Mg, Zn, K) or other supplements (e.g., St. John's Wort, echinacae, amino acids). For release/absorption control, solid carriers can be made of various component types and levels or thicknesses of coats, with or without an active ingredient. Such diverse solid carriers can be blended in a dosage form to achieve a desired performance. The liquid formulations may be delivered to, and adapted for, oral, nasal, buccal, ocular, urethral, transmucosal, vaginal, topical or rectal delivery, although oral delivery is used mostly.

When formulated with microparticles or nanoparticles, the one or more actives the release profile can easily be adapted by adding, e.g., a hard or soft gelatin coating, a starch coating, a resin or polymer coating and/or a cellulosic coating. Although not limited to microparticles or nanoparticles (as in, e.g., microcapsules or nanocapsules), such dosage forms may be further coated with, for example, a seal coating, an enteric coating, an extended release coating, or a targeted delayed release coating. The term "enteric coating" as used herein relates to a mixture of pharmaceutically acceptable excipients that is applied to, combined with, mixed with or otherwise added to the carrier or composition. The coating may be applied to an active that is compressed, molded or extruded and may also include: gelatin, and/or pellets, beads, granules or particles of the carrier or composition. The coating may be applied through an aqueous dispersion or after dissolving in appropriate solvent. The carrier may or may not be fully or partially biodegradable.

Carriers for use with the present invention include permeable and semipermeable matrices or polymers that control the release characteristics of the formulation. Such polymers include, for example, cellulose acrylates, acetates, and other semi-permeable polymers such as those described in U.S. Pat. No. 4,285,987 (hereby incorporated by reference), as well as the selectively permeable polymers formed by the coprecipitation of a polycation and a polyanioni as disclosed in U.S. Pat. Nos. 3,173,876; 3,276,586; 3,541,005; 3,541,006 and 3,546,142 (relevant portions incorporated herein by reference).

Other carriers for use with the present invention include, e.g., starch, modified starch, and starch derivatives, gums, including but not limited to xanthan gum, alginic acid, other alginates, benitoniite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, potassium polymethacrylate, carrageenan (and derivatives), gum karaya and biosynthetic gum. Other examples of useful polymers include: polycarbonates (linear polyesters of carbonic acid); microporous materials (bisphenol, a microporous poly(vinylchloride), micro-porous polyamides, microporous modacrylic copolymers, microporous styrene-acrylic and its copolymers); porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid cross-linked poly(vinylpyrrolidone).

Additional additives and their levels, and selection of a primary coating material or materials will depend on the following properties: resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; easy application as a coating (substrate friendly); and economical practicality.

Dosage forms of the compositions of the present invention can also be formulated as enteric coated delayed release oral dosage forms, i.e., as an oral dosage form of a pharmaceutical composition as described herein that uses an enteric coating to effect release in the lower gastrointestinal tract. The enteric coated dosage form will generally include microparticles, microgranules, micropellets or microbeads of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

Active Pharmaceutical Ingredients. The one or more active agents that are formulated in a self-stable manner using the present invention may include a wide variety of uses, not just the traditional pharmaceutical agents. Actives for use with the present invention in immediate and/or controlled release formulations may include systemically active therapeutic agents, locally active therapeutic agents, disinfecting agents, chemical impregnants, cleansing agents, deodorants, fragrances, dyes, animal repellents, insect repellents, fertilizing agents, pesticides, herbicides, fungicides, and plant growth stimulants, and the like. Some non-limiting examples of active agents are listed hereinbelow. Those skilled in the art will appreciate that any of these compounds may be used in the form of their pharmaceutically acceptable salt forms, e.g., carboxylic acids, with counter-ions, e.g., potassium, sodium, calcium; as ionic combinations with, e.g., resins, polymers, beads, matrices; with sugars or sugar derivatives, e.g., malate, tannate; amino acids, lipids, oils or combinations, mixtures and the like. In some embodiments, the present inventors have found that certain actives may be provided with two different salts, each of which may have a different solubility and/or release profile under, e.g., physiologic conditions. In fact, liquid formulation of present invention includes combinations of one or more of the following: immediate release, pulsatile release, controlled release, extended release, delayed release, targeted release, or targeted delayed release.

Some examples of active ingredients suitable for use in the pharmaceutical formulations and methods of the present invention include: hydrophilic, lipophilic, amphiphilic or hydrophobic, and that can be solubilized, dispersed, or partially solubilized and dispersed, on or about a carrier. The active agent-carrier combination may be coated further to encapsulate the agent-carrier combination. Alternatively, an active ingredient may also be provided separately from the solid pharmaceutical composition, such as for co-administration. Such active ingredients can be any compound or mixture of compounds having therapeutic or other value when administered to an animal, particularly to a mammal, such as drugs, nutrients, cosmaceuticals, nutraceuticals, diagnostic agents, nutritional agents, and the like. The active agents listed below may be found in their native state, however, they will generally be provided in the form of a salt. The active agents listed below include their isomers, analogs and derivatives.

In one embodiment, the active ingredient agent is hydrophobic. Hydrophobic active ingredients are compounds with little or no water solubility. Intrinsic water solubilities (i.e., water solubility of the unionized form) for hydrophobic active ingredients are less than about 1% by weight, and typically less than about 0.1% or 0.01% by weight. Suitable hydrophobic active ingredients are not limited by therapeutic category, and can be, for example, analgesics, anti-inflammatory agents, antihelmimthics, anti-arrhythmic agents, antibacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, crectile dysfunction improvement agents, immunosuppressants, anti-protozoal agents, anti-thyroid agents, anxiolytic agents, sedatives, hypnotics, neuroleptics, .beta.-Blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof. Salts, isomers and derivatives of the above-listed hydrophobic active ingredients may also be used, as well as combinations and mixtures thereof.

Other examples of suitable hydrophobic active ingredients include: acetretin, albendazole, albuterol, aminoglutethimide, amiodarone, amlodipine, amphetamine, amphotericin B, atorvastatin, atovaquone, azithromycin, baclofen, beclomethasone, benezepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donezepil, efavirenz, eposartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenyloin, frovatriptan, furazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofibran, tizanidine, topiramate, topotecan, toremifene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, and zopiclone. Of course, salts, isomers and derivatives of the above-listed hydrophobic active ingredients may also be used, as well combinations and mixtures thereof.

In other embodiments, the active ingredient is hydrophilic, however, combination of hydrophilic, hydrophobic and nonpolar agents may also be used. The water solubility for hydrophilic active ingredients is generally greater than about 0.1% by weight, and typically greater than about 1% by weight. Suitable hydrophilic active ingredients include: analgesics, anti-inflammatory agents, antihelminthics, anti-arrhythmic agents, anti-bacterial agents, anti-viral agents, anti-coagulants, anti-depressants, anti-diabetics, anti-epileptics, antifungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, .beta.-Blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof.

Other hydrophilic active ingredients include: a cytokine, a peptidomimetic, a peptide, a protein, a toxoid, a serum, an antibody, a vaccine, a nucleoside, a nucleotide, a portion of genetic material, a nucleic acid, or a mixture thereof. Other examples of suitable hydrophilic active ingredients include: acarbose; acyclovir; acetyl cysteine; acetylcholine chloride; alatrofloxacin; alendronate; aglucerase; amantadine hydrochloride; ambenomium; amifostine; amiloride hydrochloride; aminocaproic acid; amphotericin B; antihemophilic factor (human), antihemophilic factor (porcine); antihemophilic factor (recombinant), aprotinin; asparaginase; atenolol; atracurium besylate; atropine; azithromycin; aztreonam; BCG vaccine; bacitracin; becalermin; belladona; bepridil hydrochloride; bleomycin sulfate; calcitonin human; calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotaxime; cefoxitin sodium; ceftizoxime; ceftriaxone; cefuroxime axetil; cephalexin; cephapirin sodium; cholera vaccine; chorionic gonadotropin; cidofovir; cisplatin; cladribine; clidinium bromide; clindamycin and clindamycin derivatives; ciprofloxacin; clodronate; colistimethate sodium; colistin sulfate; corticotropin; cosyntropin; cromolyn sodium; cytarabine; dalteparin sodium; danaparoid; desferrioxamine; denileukin diflitox; desmopressin; diatrizoate meglumine and diatrizoate sodium; dicyclomine; didanosine; dirithromycin; dopamine hydrochloride; dornase alpha; doxacurium chloride; doxorubicin; etidronate disodium; enalaprilat; enkephalin; enoxaparin; enoxaprin sodium; ephedrine; epinephrine; epoetin alpha; erythromycin; esmolol hydrochloride; factor IX; famciclovir; fludarabine; fluoxetine; foscarnet sodium; ganciclovir; granulocyte colony stimulating factor, granulocyte-macrophage stimulating factor; growth hormones—recombinant human; growth hormone—bovine; gentamycin; glucagon; glycopyrolate; gonadotropin releasing hormone and synthetic analogs thereof, GnRH; gonadorelin; grepafloxacin; *haemophilus* B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human, insulin lispro; insulin procine; insulin NPH; insulin aspart; insulin glargine; insulin detemir; interferon alpha; interferon beta; ipratropium bromide; ifosfamide; Japanese encephalitis virus vaccine; lamivudine; leucovorin calcium; leuprolide acetate, levofloxacin; lincomycin and lincomycin derivatives; lobucavir; lomefloxacin; loracarbef, mannitol; is measles virus vaccine; meningococcal vaccine; menotropins; mepenzolate bromide; mesalamine; methenamine; methotrexate; methscopolamine; metformin hydrochloride; metoprolol; mezocillin sodium; mivacurium chloride; mumps viral vaccine; nedocromil sodium; neostigmine bromide; neostigmine methyl sulfate; neurontin; norfloxacin; octreotide acetate; ofloxacin; olpadronate; oxytocin; pamidronate disodium; pancuronium bromide; paroxetine; perfloxacin; pentamidine isethionate; pentostatin; pentoxifylline; periciclovir; pentagastrin; pentholamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymyxin B sulfate; pralidoxime chloride; pramlintide, pregabalin; propafenone; propenthaline bromide; pyridostigmine bromide; rabies vaccine; residronate; ribavarin; rimantadine hydrochloride; rotavirus vaccine; salmeterol xinafoate; sinealide; small pox vaccine; solatol; somatostatin; sparfloxacin; spectinomycin; stavudine; streptokinase; streptozocin; suxamethonium chloride; tacrine hydrochloride; terbutaline sulfate; thiopeta; ticarcillin; tiludronate; timolol; tissue type plasminogen activator; TNFR:Fc; TNK-tPA; trandolapril; trimetrexate gluconate; trospectinomycin; trovafloxacin; tubocurarine chloride; tumor necrosis factor; typhoid vaccine live; urea; urokinase; vancomycin; valacyclovir; valsartan; varicella virus vaccine live; vasopressin and vasopressin derivatives; vecuronium bromide; vinblastine; vincristine; vinorelbine; vitamin B12; warfarin sodium; yellow fever vaccine; zalcitabine; zanamivir; zolendronate; zidovudine; pharmaceutically acceptable salts, isomers and derivatives thereof, and mixtures thereof.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), anti-epileptics (e.g., phenyloin, meprobamate and nitrezepam), vasodilators (e.g., nifedipine, papaverine, diltiazem and nicardirine), anti-tussive agents and expectorants (e.g., codeine phosphate), anti-asthmatics (e.g. theophylline), antacids, anti-spasmodics (e.g., atropine, scopolamine), antidiabetics (e.g., insulin), diuretics (e.g., ethacrynic acid, bendrofluazide), anti-thypotensives (e.g., propranolol, clonidine), antihypertensives (e.g, clonidine, methyldopa), bronchodilators (e.g., albuterol), steroids (e.g., hydrocortisone, triamcinolone, prednisone), antibiotics (e.g., tetracycline), antihemorrhoidals, hypnotics, psycho-tropics, antidiarrheals, mucolytics, sedatives, decongestants, laxatives, vitamins, stimulants (including appetite suppressants such as phenylpropanolamine), as well as salts, hydrates, and solvates of the same. The above list is not meant to be exclusive.

In certain embodiments, the therapeutically active agent comprises hydromorphone, oxycodone, dihydrocodeine, codeine, dihydromorphine, morphine, buprenorphine, salts, hydrates and solvates of any of the foregoing, mixtures of any of the foregoing, and the like. In other embodiments, the active agent is a locally active therapeutic agent and the environment of use may be, e.g., the gastrointestinal tract, or body cavities such as the oral cavity, periodontal pockets, surgical wounds, the rectum or vagina. The liquid formulations of the present invention may be provided orally, topically, subcutaneously, intramuscularly, intraperitoneally, intraocularly, intraossealy, nasally, urethrally, mucosally, vaginally, rectally, intradurally, epidurally and the like. The liquid formulation of the present invention may also be provided as a mist, e.g., to the deep lung (alveolarly).

Locally active pharmaceutical agents of use with the present invention include antifungal agents (e.g., amphotericin B, clotrimazole, nystatin, ketoconazole, miconazol, etc.), antibiotic agents (penicillins, cephalosporins, erythromycin, tetracycline, aminoglycosides, etc.), antiviral agents (e.g, acyclovir, idoxuridine, etc.), breath fresheners (e.g. chlorophyll), antitussive agents (e.g., dextromethorphan hydrochloride), anti-cariogenic compounds (e.g. metallic salts of fluoride, sodium monofluorophosphate, stannous fluoride, amine fluorides) analgesic agents (e.g., methylsalicylate, salicylic acid, etc.), local anesthetics (e.g., benzocaine), oral anti-septics (e.g., chlorhexidine and salts thereof, hexylresorcinol, dequaliniurn chloride, cetylpyridinium chloride), anti-flammatory agents (e.g., dexamethasone, betamethasone, prednisone, prednisolone, triamcinolone, hydrocortisone, etc.), hormonal agents (oestriol), antiplaque agents (e.g, chlorhexidine and salts thereof, octenidine, and mixtures of thymol, menthol, methysalicylate, eucalyptol), acidity reducing agents (e.g., buffering agents such as potassium phosphate dibasic, calcium carbonate, sodium bicarbonate, sodium and potassium hydroxide, etc.), and tooth desensitizers (e.g., potassium nitrate). This list is not meant to be exclusive. Other embodiments of the present invention include disinfecting agents, e.g., chlorine compounds such as calcium hypochlorite, and the environment of use is a surrounding body of water, e.g. a recreational pool. The active may be one or more cleansing agents, a germicide, a deodorant, a surfactant, a fragrance, a perfume, a sanitize; and/or a dye, and the environment of use is an aqueous solution, e.g. a urinal or toilet bowl. Examples of fragrances include: perfume oils, volatile-compounds including esters, ethers aldehydes, alcohols, unsaturated hydrocarbons, terpenes, and other ingredients well known in the art.

The liquid formulation may also include active agents with one or more chemical agents, e.g., fertilizers, animal repellents, insect repellents, pesticides, herbicides, fungicides, plant growth stimulants, and the environment of use is, e.g., anywhere around the home, e.g. soil, trees etc. The fertilizer may be, for example, a nitrogen containing compound such as urea, urea formaldehyde composites, potassium nitrate, potassium sulfate, potassium chloride, ammonium nitrate, ammonium sulfate, monoammonium phosphate, dibasic ammonium phosphate, ammoniated super-phosphoric acid, micronutrient ingredients such as trace elements of iron, zinc, manganese, copper, boron, molybdenum, and mixtures of any of the foregoing. In these embodiments, the thickness of the controlled release coating will depend upon, among other things, the desired rate and overall time period for release of an effective amount of the active agent. In some circumstances where a relatively long time period of efficacy is desired, the substrate may be coated to a relatively high weight gain of, e.g., up to 50% or more.

The examples herein include pharmaceutically active compounds useful in the practice of the present invention, e.g., antihistamines, decongestants, antitussives and/or expectorants. Other actives for use with the present invention include, but are not limited to: non-steroidal anti-inflammatory drugs (NSAIDs) and other analgesic drugs such as acetominophen and phenacetin. These materials are incorporated into the immediate or controlled release formulations of the invention in amounts governed by the desired release characteristics of the material in such excipient base and such that conventional dosages comply with applicable federal Food and Drug Administration (FDA) or other regulations.

Decongestants useful with the present invention (along with a salt form) are phenylephrine (bitartrate, tannate, HBr, HCl), phenylpropanolamine (HCl) and pseudoephedrine (HCl). Furthermore, a number of herbal and/or natural decongestants are known in the art, all of which may be used with the present invention.

Expectorants for use with the present invention include, e.g., guaifenesin, terpin hydrate, (glyceryl guaiacolate), potassium (iodide, citrate) and potassium guaicolsulfonate. Other expectorants, whether individual ingredients or combinations of ingredients may be used with the present invention. Furthermore, a number of herbal and/or natural expectorants are known in the art, all of which may be used with the present invention, e.g., Oregano Leaf Extract 25—500 mg (which may be a liquid extract), Red Clover 25—500 mg, Buckthorn Root 25—500 mg, or Fenugreek 25—500 mg, or mixtures thereof.

Examples of antihistamines for use with the present invention (e.g., in salt form) are chlorpheniramine (maleate), brompheniramine (maleate), dexchlorpheniramine (maleate), dexbrompheniramine (maleate), triprolidine (HCl), diphenhydramine (HCl), doxylamine (succinate), tripelennamine (HCl), cyproheptatine (HCl), bromodiphenhydramine (HCl), phenindamine (tartrate), pyrilamine (maleate, tannate) and azatadine (maleate). Antitussives that may be used with the present invention (with salt form) include: caramiphen (edisylate), dextromethorphan (HBr) and codeine (phosphate, sulfate). A number of herbal and/or natural antihistamines are known in the art, all of which may be used with the present invention.

Other actives may also be included with the present invention, e.g., non-steroidal anti-inflammatory drugs (NSAIDs) such as propionic acid derivatives; acetic acid derivatives; fenamic acid derivatives; biphenylcarboxylic acid derivatives; and oxicams. Examples of propionic acid derivatives include: ibuprofen, naproxen, ketoprofen, flurbiprofen, fenoprofen, suprofen, fenbufen, and fluprofen may be mentioned as preferred compounds. Acetic acid derivatives include: tolmetin sodium, zomepirac, sulindac and indomethacin. Fenamic acid derivatives include: mefenamic acid and meclofenamate sodium. Diflunisal and flufenisal are biphenylcarboxylic acid derivatives, while oxicams include piroxicam, sudoxicam and isoxicam. Other analgesics for use with the present invention include acetominophen and phenacetin. Naproxen may be present in amounts of about 50 to about 250 milligrams per liquid dose, however, naproxen may be used in amounts of between about 100 and about 150 milligrams per liquid dose.

Phenylephrine may be present in amounts of between about 15 and about 60 milligrams per liquid dose. Phenylephrine is generally in amounts of about 5 to about 30 milligrams per liquid dose, with half or less of that amount used in a pediatric form of the formulation. In one example of the present invention, phenylephrine is provided in the amount of about 15 mg for extended release. Phenylephrine hydrochloride is an orally effective nasal decongestant. Chemically it is (S)-3-hydroxy-α[(methylamino)methyl]benzenemethanol hydrochloride. Phenylepherine is a synthetic, optically active sympathomimetic amine that has one hydroxyl group on the benzene ring. The hydroxyl group is placed in the position meta to the aliphatic side chain. The meta position affords optimal activity and phenylepherine (neo-synephrine) replaced an older preparation, synephrine, in which the hydroxyl was in the para position.

Phenylephrine hydrochloride is available in the form of the levorotatory isomer, a white, odorless, non-hygroscopic, crystalline compound possessing a bitter taste. Phenylephrine hydrochloride has a melting point of 140-145° C. and is freely soluble in water and alcohol. Decongestant compounds in the form of their free bases as well as their salts, e.g., hydrochloride, citrate, maleate, tannate, etc., are well known.

Dextromethorphan may be present in amounts of between about 5 and about 20 milligrams per liquid dose, with a general range of about 10 to about 15 milligrams. Brompheniramine may be present in amounts of between about 0.5 and about 4.0 milligrams per liquid dose with a general range of about 2.0 milligrams per liquid dose. Half or less of that amount may be used in a pediatric form of the formulation.

The present invention may also include chlorpheniramine, which is an antihistamine used to relieve, e.g., allergic rhinitis (seasonal allergy). The symptoms of allergic rhinitis include: sneezing, runny nose, itching, and watery eyes. Chlorpheniramine may also be used to treat immediate allergic reactions. Chlorpheniramine may be provided alone and in combination with other prescription or nonprescription drugs, e.g., to treat symptoms of allergy, colds, and upper respiratory infections.

The present invention may also include one or more analgesics, e.g., acetaminophen may be present in amounts of up to about 600 milligrams per liquid dose. Generally, acetaminophen is present in amounts of about 50 to about 200 milligrams per liquid dose. Another example is ibuprofen, which may be used in amounts of, e.g., 150 milligrams, with a range of about 50 and about 150 milligrams per dose being used generally. Half or less of that amount may be used in a pediatric form of the formulation.

In one example of the present invention, an expectorant (e.g., Guaifenesin DC) is provided at lower doses and is made available immediately for absorption, followed by a lower dose of a decongestant (e.g., phenylephrine) which is release slowly over, e.g., about 1 to 8 hrs. This release profile makes the product more efficacious since the large amount of expectorant begins to break up mucus prior to the time the decongestant is released to provide long acting decongestant activity after mucus breakdown has begun.

Generally, guaifenesin is present in amounts of about 10 to about 600 milligrams per liquid dose. Guaifenesin may be present in amounts of 100, 150, 200, 300, 400, 440, 500 or even 600 or more milligrams per liquid dose. In one example, guaifenesin is present in amounts of about 100 to about 200 milligrams per liquid dose, with half or less of that amount used in a pediatric form of the formulation.

In one example, 400 milligrams of guaifenesin are included as an active for immediate release. Guaifenesin is an expectorant that increases the output of phlegm (sputum) and bronchial secretions by reducing adhesiveness and surface tension. The increased flow of less viscous secretions promotes cilliary action and facilitates the removal of mucus. Hence, expectorants such as guaifenesin change a dry, unproductive cough to one that is more productive and less frequent. Guaifenesin, known chemically as 3(2-methoxyphenoxy)-1,2-propanediol, is a crystalline powder soluble in water and alcohol. It is indicated in the USP Drug information as an expectorant for the symptomatic relief of cough due to colds and minor upper respiratory infections.

Excipients for use with the present invention are well known to those of skill in the art and include humectants such as glycerin and propylene glycol, preservatives such as sodium benzoate and paraben, sweeteners such as sodium saccharin, corn syrup and sorbitol solutions, menthol and various flavoring and coloring agents. The pharmaceutically active compounds and excipients for human use should be of N.F. or U.S.P. grade.

For certain actives it may be useful to provide buffering agents (or bufferants), where the acid is a pharmaceutically acceptable acid, such as hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid, and where the base is a pharmaceutically acceptable base, such as an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, or a salt of a pharmaceutically acceptable cation and acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, and uric acid.

In some formulations additives may also include: chelating agents (such as EDTA and EDTA salts); colorants or opaquants (such as titanium dioxide, food dyes, lakes, natural vegetable colorants, iron oxides, silicates, sulfates, magnesium hydroxide and aluminum hydroxide); coolants (e.g., trichloroethane, trichloroethylene, dichloromethane, fluorotrichloromethane); cryoprotectants (such as trehelose, phosphates, citric acid, tartaric acid, gelatin, dextran and mannitol); and diluents or fillers (such as lactose, mannitol, talc, magnesium stearate, sodium chloride, potassium chloride, citric acid, spray-dried lactose, hydrolyzed starches, directly compressible starch, microcrystalline cellulose, cellulosics, sorbitol, sucrose, sucrose-based materials, calcium sulfate, dibasic calcium phosphate and dextrose).

Substrates. A powder constitutes a finely divided (milled, micronized, nanosized, precipitated) form of an active ingredient or additive molecular aggregates or a compound aggregate of multiple components or a physical mixture of aggregates of an active ingredient and/or additives. Such substrates may be formed of various materials known in the art, such as, for example: sugars, such as lactose, sucrose or dextrose; polysaccharides, such as maltodextrin or dextrates; starches; cellulosics, such as microcrystalline cellulose or microcrystalline cellulose/sodium carboxymethyl cellulose; inorganics, such as dicalcium phosphate, hydroxyapitite, tricalcium phosphate, talc, or titania; and polyols, such as mannitol, xylitol, sorbitol or cyclodextrin.

It should be emphasized that a substrate need not be a solid material, although often it will be a solid. For example, the encapsulation coat on the substrate may act as a solid "shell" surrounding and encapsulating a liquid, semi-liquid, powder or other substrate material. Such substrates are also within the scope of the present invention, as it is ultimately the carrier, of which the substrate is a part, which must be a solid.

Excipients. The solid pharmaceutical compositions suspended in the liquid formulation of the present invention may include optionally one or more additives, sometimes referred to as additives. The excipients may be contained in an encapsulation coat in compositions, which include an encapsulation coat, or can be part of the solid carrier, such as coated to an encapsulation coat, or contained within the components forming the solid carrier. Alternatively, the excipients can be contained in the pharmaceutical composition but not part of the solid carrier itself.

Solubilizers. The pharmaceutical compositions of the present invention may include optionally one or more solubilizers, i.e., additives to increase the solubility of the pharmaceutical active ingredient or other composition components in the solid carrier. It has been recognized by the present inventors that guaifenesin, in fact, acts as a solubilizer for phenylephrine, and is used as such in the examples provided herein. Other solubilizers are known in the art. Mixtures of solubilizers are also within the scope of the invention and are readily available from standard commercial sources.

The amount of solubilizer that may be included in compositions of the present invention is not particularly limited. Of course, when such compositions are administered to a patient, the amount of a given solubilizer is limited to a bioacceptable amount, which is readily determined by one of skill in the art. In some circumstances, it may be advantageous to include amounts of solubilizers far in excess of bioacceptable amounts, for example, to maximize the concentration of active ingredient, with excess solubilizer removed prior to providing the composition to a patient using conventional techniques, such as distillation or evaporation.

The following are general instructions common to most liquid manufacturing as will be known to the skilled artisan. For example, first, it is determined is all of the raw materials are available for this manufacturing process. All of the raw materials are checked for correct identity and Quality Assurance release. All personnel involved in the manufacturing process must be familiar with the active ingredients Material Safety Data Sheet and for those involved in the manufacturing process, these must wear appropriate attire and use the appropriate safety equipment. Standard microbiological precautions are followed, e.g., avoidance of contact with the raw materials and use of gloves during the manufacturing process. When using water, water purity is verified and use of a Purified Water System is recommended. Prior to use allow the water to run to waste for 15 seconds. Assure that the water quality is greater than 14 megohm-cm (MΩ-cm) on the second deionized water finishing tank.

Example 1

APAP-Hydrocodone Suspensions

A suspension formulated using the Hydrocodone Bitartarate Polistirex (Ion Exchange resin Drug complex) and Acetaminophen (APAP) was studied. Briefly, the APAP 500 mg/5 ml dose, (purchased from Rhodia Inc, Cranburry, N.J., 08512, USA) was added in the formulation of Hdyrocodone Bitartarate Polistirex (Drug Resin conjugate) suspension. These suspension formulations were made in the Pharmafab Research and Development laboratory. It was expected that the APAP would release quickly and there would be a sustained release of the Hydrocodone. The dose of Hydrocodone is 10 mg/5 ml. It is expected that if 50% to 60% of the Hydrocodone is released in the first hour then, the therapeutic effectiveness of the combination can be increased when given with immediate release APAP (as designed in this formulation). Since in this formulation the Hydrocodone resin conjugate is coated with sustained release coating material (Ethyl cellulose), the release of Hydrocodone is based on two factors. First, the availability of ions to replace the ion exchange resin sites which cause the release of Hydrocodone and secondly the diffusion of Hydrocodone molecules from the coating material to the absorption sites, when administered orally. It is known that the release of Hydrocodone in the first hour is crucial for the therapeutic effect, but the coating and non availability of the ions in the system make the initial Hydrocodone release delayed. This release may not reach the desired 50% release of drug for efficient therapeutic efficacy. The presence of ions is required for the release of Hydrocodone from the ion exchange resin. It was found that by addition of ionic salts, this first hour release can be modified as disclosed below.

A suspension of APAP 500 mg and Hydrocodone 10 mg per 5 ml was prepared using Xanthan gum (purchased from Rhodia Inc, Cranburry, N.J., 08512, USA) as the suspending agent and several other ingredients such as color, flavor, parabens (e.g., methylparaben abd propylparaben)(preservatives), high fructose corn syrup (viscosity builder and sweetener), propylene glycol (solvent and dispersing agent), and ascorbic acid (to adjust the pH of the suspension) were used to achieve a stable suspension. The Hydrocodone Bitartarate was conjugated with IRP 69 resin (purchased from Coating Place Inc, Wisconsin, USA) and the conjugate was coated with a sustained release material (ethyl cellulose) in Coating Place Inc's fluid bed coater. The suspensions were studied for release profiles in 0.1 N HCl at pH 1.2 using USP dissolution apparatus II with 900 ml of dissolution medium. Samples were withdrawn at predetermined time intervals and were analyzed for APAP and Hydrocodone content using HPLC analysis. The release of drug against time was plotted.

Different amounts of salt (Sodium chloride—Purchased from J T Baker, Phillisburg, N.J., 08865, USA) were added to three suspensions to obtain suspensions with varying salt concentrations (Sodium chloride concentration at 0.1, 0.3, and 0.5%). The suspensions were mixed and held for 24 hours to achieve equilibrium. The salt-added suspensions were studied for release profiles at pH 1.2 and these drug release profiles were compared. The results are given in Table 1 and FIG. 1.

TABLE 1

Drug release in first one hour from the suspensions with and without the salt addition.

| Time | 0.25 hr | 0.5 hr | 1.0 hr |
|---|---|---|---|
| APAP-HCB Suspension | n/a | 16.5 | 20.5 |
| Suspension with 0.1% Salt | 48.1 | 51.7 | 62.4 |
| Suspension with 0.3% Salt | 58.0 | 62.9 | 65.9 |
| Suspension with 0.5% Salt | 71.0 | 71.5 | 78.9 |

FIG. 1 shows the release of the Hydrocodone for 10 hours in a sustained release suspension showing the impact of the added salt on the comparatively faster release of the dug from the coated Hydrocodone Polistirex.

It is observed that the first hour release of the drug can be controlled by the addition of various amounts of salt. In the case of APAP-Hydrocodone Suspension, it was observed that there was gradual increase in release at the first hour with an increase in the amount of salt added. For a suspension containing 0.1% salt the release was 62.4%, for 0.3% it was 65.9%, and for 0.5% it was 78.9%. The release of the suspension that contained no salt was only 20.5% at 1 hour.

Example 2

Tussionex® Marketed Product Study

A similar study was conducted using the marketed Tussionex product that contains Hydrocodone Polistirex equivalent to Hydrocodone Bitartarate (HCB) 10.0 mg/5 ml and Chlorpheniramine Polistirex equivalent to Chlorpheniramine Maleate (CPM) 8.0 mg/5 ml. Dissolution studies were per-formed on this marketed suspension with and without the addition of Sodium chloride. (Sodium chloride, Purchased from J T Baker, Phillisburg, N.J., 08865, USA, was added at a level of 0.3%) These suspensions were studied for release profiles in 0.1 N HCl at pH 1.2 using USP dissolution apparatus II with 900 ml of dissolution medium. Samples were withdrawn at predetermined time intervals and were analyzed for APAP and Hydrocodone content using HPLC analysis. The release of drug against time was plotted.

Figure 2:
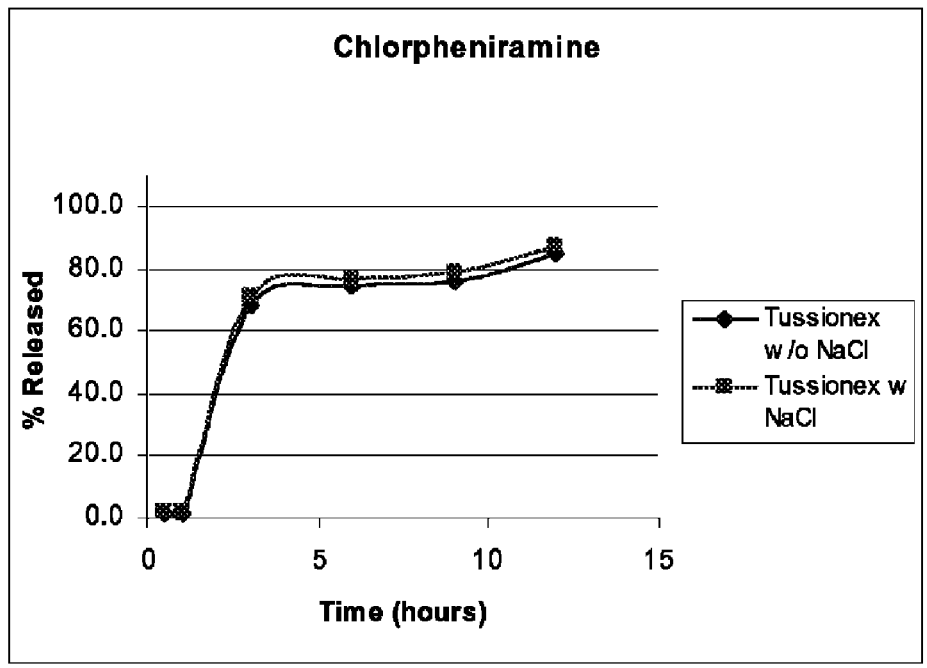
FIG. 2 is a graph that shows CPM release over 12 hours from the suspension with and without the salt addition.
Figure 3:
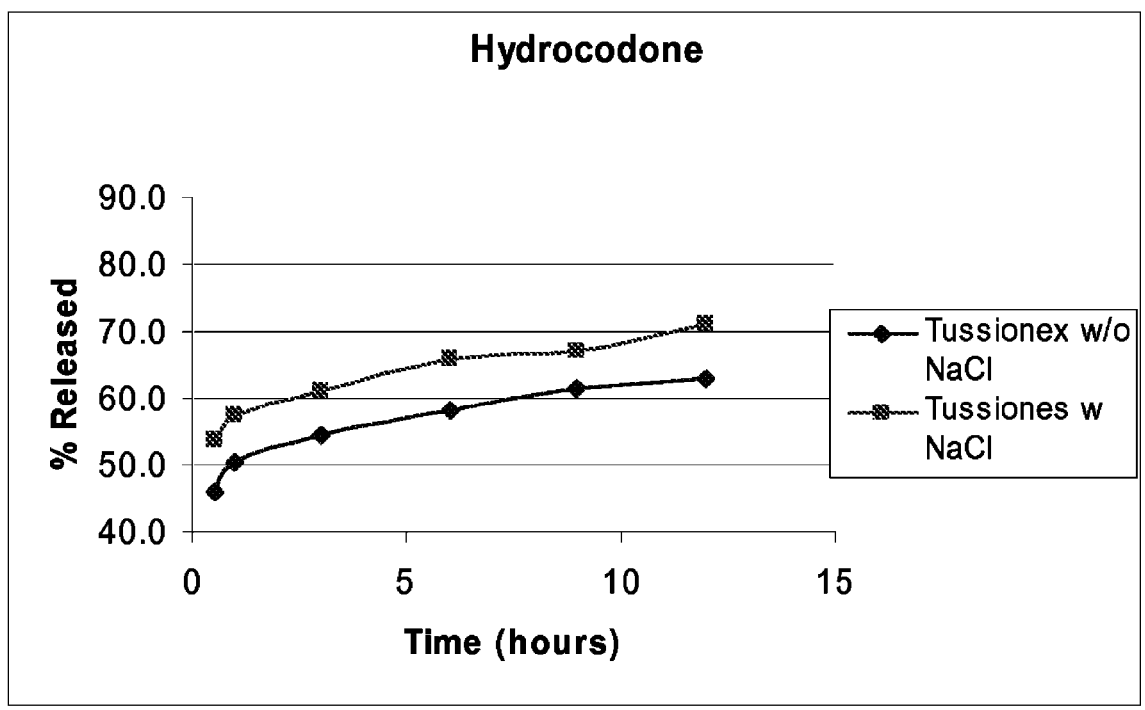
FIG. 3 is a graph that shows HCB release over 12 hours from the suspension with and without the salt addition.

The first hour and 12 hour release of the drug was studied. The results are given in following table 2 and FIG. 2 for CPM and FIG. 3 for HCB

TABLE 2

Drug release from the Marketed Tussionex suspension with and without salt addition.

| % drug released | CPM | CPM | HCB | HCB |
|---|---|---|---|---|
| Time | 0.5 hr | 1.0 hr | 0.5 hr | 1.0 hr |
| Tussionex Suspension | 1.2 | 1.7 | 46.3 | 50.2 |
| Suspension with 0.3% Salt | 2.5 | 2.4 | 53.9 | 57.3 |

It is observed that the first hour release of the drug can be increased by the addition of salt. For the marketed product the release increased from 50.2% to 57.3% in the first hour with the addition of salt (Sodium chloride concentration at 0.3%).

Similar control over the drug release can be achieved from the suspensions using the drug Polistirex conjugate in following drugs and many other salts like Potassium Chloride and other monovalent ionic salts, Calcium chloride, and other divalent ionic salts and Aluminum Chloride and similar trivalent ionic salts, will with different valances will also have varying impacts on the drug release from such drug resin conjugates with or without coating. As these salts will be providing different amount of ionic moieties for replacements of the drug from the drug resin conjugates.

TABLE 3

Various Drug suspension which can show better drug release in the first hour due to addition of the salts.

| Drug | Dosage Form |
|---|---|
| Phenylephrine HCl | Coated/Uncoated |
| Chlorpheniramine | Uncoated/Coated Sorbital Treatment Coated |
| Dextromethorphan HBr | Coated |
| Pseudoefedrine HCL Polistirex | Uncoated/Coated |
| Ibuprofen Polistirex | Uncoated/Coated |
| APAP/HCR Polistirex | Uncoated/Coated |
| CPM/HCR Polistirex | Uncoated/Coated |
| Promethazine/HCR | Uncoated/Coated |
| Loratidine Polistirex | Uncoated/Coated |

The following list of formulation can be modified using the present invention.
1. Phenylephrine HCl, (PHE) coated and uncoated suspension
2. Chlorpheniramine Maleate (CPM) coated and uncoated suspension
3. Dextromethorphan HBr (DEX) Coated suspension
4. Pseudoefedrine HCl (PSE) Uncoated suspension
5. Ibuprofen (IBU) Polistirex uncoated suspension
6. Loratidine (LRT) Polistirex uncoated suspension
7. Hydrocodone Bitartarate (HCR) Polistirex coated suspension
8. Promethazine (PMT) Polistirex uncoated suspension
9. Possible combination suspensions where the first hour release can be altered by salt addition:
    a. CPM/HCR
    b. PHE/IBU
    c. PSE/HCR
    d. DEX/PSE
    e. PMT/HCR
    f. CPM/DEX
    g. DEX/HCR
    h. LRT/IBU It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for modifying the release of at least one pharmacologically active drug from a coated drug-ionic resin in a controlled-release liquid formulation comprising:
    adding one or more ionic salts to a controlled-release oral liquid formulation comprising one or more coated drug-ionic resins loaded with one or more pharmacologically active drugs, wherein the addition of said one or more ionic salts increases the amount of at least one pharmacologically active drug released from the drug-ionic resin in the first hour as observed in vitro.

2. The method of claim 1, wherein the one or more drug-ionic resins are coated with a water-permeable diffusion barrier.

3. The method of claim 1, wherein one or more pharmacologically active drugs comprise both an immediate release pharmacologically active drug and an extended release pharmacologically active drug.

4. The method of claim 1, wherein the drug-ionic resins further comprise one or more polymers selected from the group consisting of cellulose, ethylcellulose, methylcellulose, propylcellulose, methoxypropylcellulose, cellulose nitrate, poly(vinyl alcohol), poly(vinyl chloride), polystyrene, polyethylene, polypropylene, poly(ethylene-co-vinyl acetate), poly(hydroxybutyric acid), poly(hydroxyvalerianic acid-co-hydroxybutyric acid), poly(lactic acid), poly(glycolic acid), poly(lactic acid-co-glycolic acid), poly($\epsilon$-caprolactones), poly($\epsilon$-caprolactone-co-DL-lactic acid), poly(maleic anhydride), polyamides, gelatin, chitosan, collagen, poly(hydroxyalkyl)-L-glutamines, poly($\gamma$-ethyl-L-glutaminate-co-glutamic acid), poly(L-leucine-co-L-aspartic acid), poly(proline-co-glutamic acid), poly(alkyl 2-cyanoacrylates), polyurethanes, poly(methyl methacrylate), poly(methyl methacrylate-co-methacrylic acid) and poly(methacrylate-co-hydroxypropyl methacrylate), polystyrene, polistirex, salts, combinations and mixtures thereof.

5. The method of claim 1, wherein the ionic salt comprises an inorganic salt.

6. The method of claim 1, wherein the ionic salt is sodium chloride.

7. The method of claim 1, wherein the oral liquid formulation comprises a first pharmacologically active drug and a second pharmacologically active drug and the one or more ionic salts modify the release profile of the first pharmacologically active drug but not the second pharmacologically active drug.

8. The method of claim 1, wherein the one or more pharmacologically active drugs comprises phenylephrine HCl.

9. The method of claim 1, wherein the one or more pharmacologically active drugs comprises chlorpheniramine maleate.

10. The method of claim 1, wherein the one or more pharmacologically active drugs comprises dextromethorphan HBr.

11. The method of claim 1, wherein the one or more pharmacologically active drugs comprises ibuprofen polistirex.

12. The method of claim 1, wherein the one or more pharmacologically active drugs comprises loratidine polistirex.

13. The method of claim 1, wherein the one or more pharmacologically active drugs comprises hydrocodone bitartarate polistirex.

14. The method of claim 1, wherein the one or more pharmacologically active drugs comprises chlorpheniramine maleate and hydrocodone bitartarate polistirex.

15. The method of claim 1, wherein the one or more pharmacologically active drugs comprises pseudoefedrine HCl.

16. The method of claim 1, wherein the one or more pharmacologically active drugs comprises promethazine.

17. The method of claim 3, wherein the one or more pharmacologically active drugs comprises chlorpheniramine maleate and hydrocodone bitartarate polistirex.

18. The method of claim 1, wherein the release of said amount is measured in a dissolution assay using a USP dissolution apparatus II with 900 ml of 0.1N HCl dissolution medium at pH 1.2.

19. A controlled-release oral liquid composition comprising one or more coated drug-ionic resins loaded with one or more pharmacologically active drugs, wherein the oral liquid composition is improved by increasing the ionic strength of the oral liquid composition by addition of one or more ionic salts whereby the amount of at least one pharmacologically active drug released from the drug-ionic resin in the first hour is increased as observed in vitro.

20. The composition of claim 19, wherein the one or more drug-ionic resins are coated with a water-permeable diffusion barrier.

21. The composition of claim 19, wherein one or more pharmacologically active drugs comprise both an immediate release pharmacologically active drug and an extended release pharmacologically active drug.

22. The composition of claim 19, wherein the drug-ionic resins further comprise one or more polymers selected from the group consisting of cellulose, ethylcellulose, methylcellulose, propylcellulose, methoxypropylcellulose, cellulose nitrate, poly(vinyl alcohol), poly(vinyl chloride), polystyrene, polyethylene, polypropylene, poly(ethylene-co-vinyl acetate), poly(hydroxybutyric acid), poly(hydroxyvalerianic acid-co-hydroxybutyric acid), poly(lactic acid), poly(glycolic acid), poly(lactic acid-co-glycolic acid), poly($\epsilon$-caprolactones), poly($\epsilon$-caprolactone-co-DL-lactic acid), poly(maleic anhydride), polyamides, gelatin, chitosan, collagen, poly(hydroxyalkyl)-L-glutamines, poly($\gamma$-ethyl-L-glutaminate-co-glutamic acid), poly(L-leucine-co-L-aspartic acid), poly(proline-co-glutamic acid), poly(alkyl 2-cyanoacrylates), polyurethanes, poly(methyl methacrylate), poly(methyl methacrylate-co-methacrylic acid) and poly(methacrylate-co-hydroxypropyl methacrylate), polystyrene, polistirex, salts, combinations and mixtures thereof.

23. The composition of claim 19, wherein the ionic salt comprises an inorganic salt.

24. The composition of claim 19, wherein the ionic salt is sodium chloride.

25. The composition of claim 19, wherein the oral liquid formulation comprises a first pharmacologically active drug and a second pharmacologically active drug and the one or more ionic salts modify the release profile of the first pharmacologically active drug but not the second pharmacologically active drug.

26. The composition of claim 19, wherein the one or more pharmacologically active drugs comprises chlorpheniramine maleate and hydrocodone bitartarate polistirex.

27. The composition of claim 21, wherein the one or more pharmacologically active drugs comprises chlorpheniramine maleate and hydrocodone bitartarate polistirex.

28. The composition of claim 19, wherein the release of said amount is measured in a dissolution assay using a USP dissolution apparatus II with 900 ml of 0.1N HCl dissolution medium at pH 1.2.

* * * * *